United States Patent [19]
Iida et al.

[11] Patent Number: 6,077,941
[45] Date of Patent: Jun. 20, 2000

[54] METHOD FOR PRODUCING 1,2-NAPHTHOQUINONE-2-DIAZIDE DERIVATIVES

[75] Inventors: Hirotada Iida, Tokyo; Nobuhiro Yoneyama, Saitama; Seiju Tobishima, Chiba; Toshio Itahana, Tokyo; Kunihiko Kojima, Chiba, all of Japan

[73] Assignee: Toyo Gosei Kogyo Co., Ltd., Chiba, Japan

[21] Appl. No.: 09/333,785

[22] Filed: Jun. 15, 1999

[51] Int. Cl.$^7$ .................................................. C07C 245/00
[52] U.S. Cl. ........................................... 534/556; 534/557
[58] Field of Search ...................... 534/556, 557

[56] References Cited

U.S. PATENT DOCUMENTS 5,192,640  3/1993  Scheler et al. ..................... 534/557

*Primary Examiner*—Fiona T. Powers
*Attorney, Agent, or Firm*—Huntley & Associates

[57] ABSTRACT

An effective method for producing a 1,2-naphthoquinone-2-diazide or a sulfo-substituted compound thereof from a 2-diazo-1-naphthalenesulfonic acid or a sulfo-substituted compound thereof. A 1,2-naphthoquinone-2-diazide derivative or a sulfo-substituted compound thereof is derived from a 2-diazo-1-naphthalenesulfonic acid or a sulfo-substituted compound thereof by use of an aqueous alkaline solution containing iodine; an aqueous alkaline solution containing iodine which is dissolved in an organic solvent; or an aqueous alkaline solution containing an oxidizing agent and iodine or an iodine compound.

8 Claims, No Drawings

METHOD FOR PRODUCING 1,2-NAPHTHOQUINONE-2-DIAZIDE DERIVATIVES

BACKGROUND OF THE INVENTION

The present invention relates to a process for producing a 1,2-naphthoquinone-2-diazide derivative, such as 1,2-naphthoquinone-2-diazide, a salt of 1,2-naphthoquinone-2-diazide-5-sulfonic acid, or that of 1,2-naphthoquinone-2-diazide-6-sulfonic acid, which is important as a starting material for preparing an azo dye, a photosensitive component of radiation-sensitive positive-type photoresist compositions, a positive-type photosensitive lithographic printing plate, etc.

BACKGROUND ART

Among 1,2-naphthoquinone-2-diazide and its sulfo-substituted compounds the compound of greatest industrial importance is sodium 1,2-naphthoquinone-2-diazide-5-sulfonate having a chemical structure represented by the following formula (I):

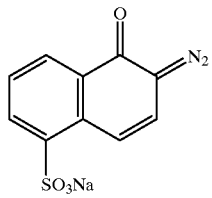

(1)

According to "Chemical Abstracts" published by the American Chemical Society, this compound is named sodium 6-diazo-5,6-dihydro-5-oxo-1-naphthalenesulfonate. The CAS registry number of the sodium salt is "2657-00-3" and that of the free sulfonic acid thereof is "20546-03-6." With regard to method for producing 1,2-naphthoquinone-2-diazide or a sulfo-substituted compound thereof on an industrial scale, the following two methods (a) and (b) are known:

(a) a method in which 2-amino-1-hydroxynaphthalene or a sulfo-substituted compound thereof is diazotized in the presence of a heavy metal salt such as a salt of copper, iron, nickel, or zinc; and (b) a method in which 2-amino-1-naphthalenesulfonic acid or a sulfo-substituted compound thereof is diazotized and the resultant 2-diazo-1-naphthalenesulfonic acid or a sulfo-substituted compound thereof is treated in an alkaline solution.

The above method (a) is suitable for producing a starting material for an azo dye. However, since the product is contaminated with a heavy metal it is not suitable for producing materials for forming a photoresisit. Thus, a salt of 1,2-naphthoquinone-2-diazide-5-sulfonic acid, which is the most important starting material for producing a photosensitive agent in a positive-type photoresist, is usually produced by use of method (b). A salt of 1,2-naphthoauinone-2-diazide-6-sulfonic acid can also be produced by use of the same method.

For more than ninety years it has been known that a salt of 1,2-naphthoquinone-2-diazide-5-sulfonic acid is derived from a salt of 2-diazo-1,5-naphthalenedisulfonic acid in an alkaline aqueous solution. DE-PS160536 (1904) and DE-PS162009 (1904) (Badiche Amilin-&Soda-Fabrik) disclose that the co-presence of an oxidizing agent such as sodium hypochlorite improves the yield of 1,2-naphthoquinone-2-diazide-5-sulfonate in the above reaction. However, the subject of these patents is drawn to production of a starting material for preparing an azo dye. Any of the currently performed methods for producing a salt of 1,2-naphthoquinone-2-diazide-5-sulfonic acid serving as a starting compound for preparing a photosensitive material used in positive-type photoresists is considered to be almost identical with these classical methods. However, very few documents have been published so far which disclose a method for producing the sulfonate, and therefore the details remain unknown. However, the study of Wolter, Gerhard and Junghans, Dieter, et al. has been disclosed in Ger. (East) DD 221,174 (1985) relatively recently. The patent discloses a method for producing a sodium 1,2-naphthoquinone-2-diazide-5-sulfonate, and in particular focuses on control of the redox potential of a species in a reaction mixture and pH of the reaction mixture so as to fall within predetermined ranges during processing of a sodium 2-diazo-1,5-naphthalenedisulfonate by use of an aqueous alkaline solution containing sodium hypochlorite. Thus, no fundamental progress in methodology is seen in the method for producing the 5-sulfonate described in the patent. In addition, from working examples in the patent the yield of 1,2-naphthoquinone-2-diazide-5-sulfonate is poor.

Meanwhile, although 1,2-naphthoquinone-2-diazide (CAS registry number 879-15-2) has industrial value as a starting compound for a photosensitive material used in a photoresist or the like, no effective industrial method for production has yet been established. J. Prak. Chem. Vol. 105 (1922/23), 257E, Bamberger et al. discloses a method in which a diazotized product of 2-naphthylamine is reacted with a cool aqueous solution containing sodium hydroxide and potassium ferricyanide to thereby obtain 1,2-naphthoquinone-2-diazide with an excellent yield. However, the method is not suitable for producing a photosensitive material applicable to a photoresist,1 since the 2-naphthylamine and potassium ferricyanide used in the method are toxic, and the obtained 1,2-naphthoquinone-2-diazide is contaminated with iron ions. Other methods such as a method in which 2-naphthol is condensed with p-toluenesulfonylazide (J. M. Tedder et al., J. Chem. Soc., 1960, 4417) and a method in which 1,2-naphthoquinone is condensed with p-tolueneslfonylhydrazide (J. M. Hacker et al., J. Am. Chem. Soc., 115, 5410 (1993)) are not suitable as industrial processes in that the yield of the target 1,2-naphthoquinone-2-diazide is unsatisfactory. The above-described Ger. (East) DD 221,174 1,1-985) shows a working example concerning production of 1,2-aphthoquinone-2-diazide. However, the yield thereof is as low as 63%.

As described herein above, methodology for producing a 1,2-naphthoquinone-2-diazide derivative has not seen any progress for a long time, although the derivative is of industrial importance.

SUMMARY OF THE INVENTION

The present invention provides a method for producing a 1,2-naphthoquinone-2-diazide derivative, which method comprises bringing a 2-diazo-1-naphthalenesulfonic acid derivative into contact with an aqueous alkaline solution.

The present method solves the problems and is based on the disvery that, in a process for producing a 1,2-naphthoquinone-2-diazide derivative by bringing a 2-diazo-1 -naphthalenesulfonic acid derivative into contact with an aqueous alkaline solution incorporating of iodine or an iodine compound into the alkaline solution results in an excellent yield of the target product.

Accordingly, in one aspect of the present invention, there is provided a method for producing a 1,2-naphthoquinone-2-diazide derivative, which method comprises bringing a 2-diazo-1-naphthalenesulfonic acid derivative into contact with an aqueous alkaline solution containing at least one substance selected from the group consisting of iodine and iodine compounds.

Preferably, the aqueous alkaline solution contains iodine.

Preferably, the aqueous alkaline solution comprises a mixture of an alkaline aqueous solution and iodine dissolved in an organic solvent which is hardly soluble in water and which exhibits little reactivity with iodine.

Preferably, the aqueous alkaline solution containing at least one substance selected from among iodine and iodine compounds further contains an oxidizing agent.

Preferably, the 1,2-naphthoquinone-2-diazide derivative produced by the method according to the present invention is 1,2-naphthoquinone-2-diazide, and; sodium, potassium, magnesium, calcium, barium, aluminium, trimethylammonium, triethylammonium, tetramethylamonium, or tetraethylammonium salts of the following sulfonic acids; 1,2-naphthoquinone-2-diazide-5-sulfonic acid, 1,2-naphthoquinone-2-diazide-6sulfonic acid, 1,2-naphthoquinone-2-diazide-7-sulfonic acid, 1,2-naphthoquinone-2-diazide-5,6-disulfonic acid, 1,2-naphthoquinone-2-diazide-5,7-disulfonic acid, or 1,2-naphthoquinone-2-diazide-5,8-disulfonic acid. As described above, although a salt of 1,2-naphthoquinone-2-diazide-5-sulfonic acid is industrially important among these naphthoquinonediazide compounds, 1,2-naphthoquinone-2-diazide is also of great value. Needless to say, these compounds should not be construed as limiting the invention thereto.

DETAILED DESCRIPTION OF THE INVENTION

As used herein, the expression "2-diazo-1-naphthalenesulfonic acid derivative" encompasses 2-diazo-1-naphthalenesulfonic acid, a sulfo-substituted compound thereof, salt end sulfa substrated compounds of 2-diazo-1-naphthalanesulfonic acid as well as others possible substitution derivatives.

The method of the present invention may be categorized into three types; i.e., methods 1 to 3, in accordance with the manner for incorporating iodine or an iodine compound into the above-described aqueous alkaline solution. In method 1, a 2-diazo-1-naphthalenesulfonic acid derivative is brought into contact with an aqueous alkaline solution containing iodine. In method 2, a 2-diazo-1-naphthalenesulfonic acid derivative is brought into contact with a mixture of an alkaline solution and iodine dissolved in an organic solvent which is hardly soluble in water and which has little reactivity with iodine. In method 3, a 2-diazo-1-naphthalenesulfonic acid derivative is brought into contact with an aqueous alkaline solution containing an oxidizing agent and at least one substance selected from among iodine and iodine compounds.

No particular limitation is imposed on the aqueous alkaline solution employed in the above methods 1 to 3, and a wide range of aqueous alkaline solutions may be used. A particularly effective solution is one which is obtained by dissolving or dispersing in water one or more substances selected from among sodium hydroxide, potassium hydroxide, sodium carbonate, potassium carbonate, magnesium oxide, and magnesium hydroxide.

As described above, method 1 employs an aqueous alkaline solution containing iodine. Iodine is added in an amount of 80–150 mol %, preferably 100–120 mol %, based on a starting 2-diazo-1-naphthalenesulfonic acid derivative.

Method 2 employs a mixture of an aqueous alkaline solution and iodine dissolved in an organic solvent. No particular limitation is imposed on the organic solvent, and a variety of organic solvents may be used so long as they permit free dissolution of iodine therein, suppress reaction between iodine and an alkali substance, and exhibit poor solubility in water. Examples of the solvents include benzene; monoalkylbenzenes such as toluene and ethylbenzene; dialkylbenzenes such as xylene and diethylbenzene; trialkylbenzenes such as mesitylene; aryl halides such as chlorobenzene, dichlorobenzene, and chlorotoluene; ethers such as ethyl ether, isopropyl ether, and butyl ether; and alkyl halides such as chloroform, dichloromethane, dichloroethane, and trichloroethane. These solvents may be used singly or in combination of two or more species. The amount of iodine which is added in method 2 is the same as described for method 1.

Method 3 employs an aqueous alkaline solution containing an oxidizing agent and at least one substance selected from among iodine and iodine compounds. Examples of the iodine compounds include iodides of metals such as lithium, sodium, potassium, calcium, and aluminum; hypoiodite or iodate salts; hydroiodides of amine such as trimethylamine or triethylamine; iodide salts of tetraalkylammonium such as tetramethylammonium or tetraethylammonium; iodine halides such as iodine chloride, iodine bromide, and iodine trichioride; and iodine oxides such as diiodine tetraoxide and diiodine pentaoxide. The iodine compounds and iodine may be used singly or in a combination of two or more species.

Examples of the oxidizing agent include chlorine, bromine, sodium hypochlorite, potassium hypochlorite, calcium hypochlorite, magnesium hypochlorite, sodium hypobromite, potassium hypobromite, hydrogen peroxide, potassium permanganate, and sodium permanganate. The oxidizing agents may be used singly or in a combination of two or more species.

In method 3, although the amount of iodine or an iodine compound may vary depending on the species thereof, iodine or an iodine compound is added typically in an amount of 0.5–50 mol %, preferably 3–30 mol %, based on a starting 2,-diazo-1-naphthalenesulfonic acid derivative. In addition, although the amount of the oxidizing agent may vary depending on the species, the oxidizing agent is added typically in an amount of 80–150 mol %, preferably 100–120 mol %, as reduced to active oxygen based on a starting 2-diazo-1-naphthalenesulfonic acid derivative.

As described above, these three methods 1 through 3 have different features. However, these three methods share the same basic procedure, which will next be described.

1. Outline of Production Method

A 2-amino-1-naphthalenesulfonic acid derivative is diazotized by the use of sodium nitrite and hydrochloric acid, or sodium nitrite and sulfuric acid, to obtain an aqueous suspension of 2-diazo-1-naphthalenesulfonic acid or a sulfosubstituted compound thereof. Excess acids contained in the suspension are neutralized. In method 1 described above, pulverized iodine crystals are added thereto, while in method 2, iodine dissolved in an organic solvent is added thereto. An aqueous alkaline solution is added dropwise to maintain the pH within the range of 8–12. After the diazonium salt disappears, the target compound is separated by salting out or by use of an acid. In method 3, after neutralization of an aqueous suspension of a diazo compound obtained in the same manner as described above, a suitable amount of iodine or iodine compound is added thereto. A water soluble oxidizing agent and an aqueous alkaline solution are also added thereto. The pH of the reaction mixture is maintained at 8–12. After completion of the reaction, the target compound is separated in the same manner as described above.

2. Volume of the Reaction Mixture

The volume of the reaction mixture greatly depends on the level of water-solubility and the amount of the starting 2-amino-1-naphthalenesulfonic acid derivative and a diazco compound obtained therefrom. For example, starting materials such as 2-amino-1-naphthalenesulfonic acid, 2-amino-1,6-naphthalenedisulfonic acid, as well as diazo compounds obtained therefrom. for example, starting materias such as 2-amino-1-naphthalensulfonic acid, 2-amino-1,6-naphthlendisulfonic acid, as well as diazo compounds thereof are sparingly soluble in water, and therefore a reverse diazotization method is suitable for effecting diazotization. Although reverse diazotization results in an increase in the volume of the entirety of the reaction mixture, the products of the reaction, i.e., 1,2-naphthoquinone-2-diazide, sodium 1,2-naphthoquinone-2-diazide-6-sulfonate, and so forth, are also sparingly soluble in water, and thus the product can be easily separated even when the volume of the reaction system increases.

3. Reaction Temperature

The method according to the present invention can be performed within a wide temperature range, typically 0–40° C. In general, the reaction rate of the method is low at low temperatures, whereas at high temperatures side reactions occur significantly. However, the yield of the target compound produced through the method according to the present invention is less susceptible to variation o temperature as compared with the case in which 1,2-naphthoquinone-2-diazides are produced without use of iodine or an iodine compound.

4. pH of the Reaction Mixture

In the method according to the present invention a predominant reaction comprises a step for converting a 2-diazo-1-naphthalenesulfonic acid or a sulfo-substituted compound thereof to a 1,2-naphthoquinone-2-diazide or a sulfc-substituted compound thereof. Preferably, the pH of a reaction mixture during this predominant reaction is 8–12, most preferably 8.5–11.

The present invention will next be described by way of examples, which should not be construed as limiting the invention thereto.

EXAMPLE 1

A monosodium salt of 2-amino-1,5-naphthalenedisulfonic acid (0.1 mol) was dispersed and dissolved in water (200 g). Into this solution concentrated hydrochloric acid (0.13 mol) was added. An aqueous 30% sodium nitrite solution (23.5 g) was also added dropwise at 5–10° C. for diazotization. After the mixture was stirred at 10–15° C. for one hour amidosulfuric acid was added thereto to thereby decompose excess nitrous acid.

An aqueous solution of 35% sodium hydroxide was added dropwise into the reaction mixture so as to adjust the pH of the system to 10–10.7. Under vigorous agitation, pulverized iodine crystals (26 g) were added to the reaction mixture. An aqueous 35% sodium hydroxide solution (45 g) was added dropwise over 3.5 hours so as to adjust the temperature and the pH of the reaction mixture to 8–13° C. and 10.5–10.8 respectively. After sodium 2-diazo-1,5-naphthalenedisulfonate was confirmed to have disappeared hydrochloric acid was added to the reaction mixture so as to adjust the pH to 7–8. Sodium chloride (60 g) was added portionwise thereto and the reaction mixture was cooled to 14–15° C. Subsequently, the resultant mixture was filtered under reduced pressure. The residue was washed with a 10° C. solution prepared by dissolving potassium iodide (1 g) and sodium chloride (2 g) in water (22 g, 10°), followed by drying in a blower drier at 45° C. to thereby obtain 26.9 g of sodium 1,2-naphthoquinone-2-diazide-5-sulfonate in the form of microcrystals (purity: 89.5%). This yield corresponds to 88.1% of the theoretical yield from the starting material employed, monosodium salt of 2-amino-1,5-naphthalenedisulfonic acid.

To a filtrate (375 g) from which the microcrystalline product had been separated, water (100 g) was added, and pH was adjusted to 1.5 with sulfuric acid. Chlorine (7.5 g) was caused to be absorbed into the mixture at 20–25' C. Iodine crystals that precipitated were separated from the mixture by filtration, washed, and dried. The yield of iodine was 22.8 g, which corresponds to 87.7% recovery of iodine used as the starting material.

EXAMPLE 2

A monosodium salt of 2-amino-1,5-naphthalenedisulfonic acid (0.1 mol) was diazotized in the same manner as in Example 1. The pH of the reaction mixture was regulated. Iodine (26 g) was dissolved in mesitylene (130 g), and the resultant solution was added to the reaction mixture. The subsequent procedure is similar to that in Example 1. That is, an aqueous sodium hydroxide solution was added dropwise so as to transform a monosodium salt of 2-diazo-1,5-naphthalenedisulfonic acid into sodium 1,2-nadhthoquinone-2-diazide-5-sulfonate. Subsequently, sodium chloride was added. A target product in the form of microcrystals was obtained through salting out, filtration, washing, and drying. The theoretical percentage recovery of the target product is 89.3%.

In the filtrate, sodium iodide (approximately 0.2 mol) was present as dissolved therein. The filtrate was processed through the following method so as to recover iodine. Briefly, an aqueous 35% hydrogen peroxide solution (10 g) was diluted with water (200 g), and the resultant solution was added to the filtrate. The resultant mixture was cooled to 10° C. at 25% Sulfuric acid (60 g) was added thereto, and the mixture was stirred for two hours at 10° C. Iodide ions were oxidized and converted to elemental iodine. Elemental iodine (22 g) as dissolved in mesitylene came to float on the surface of the aqueous mixture. The iodine in mesitylene was able to be reused for the above synthesis reaction.

EXAMPLE 3

A monosodium salt of 2-amino-1,5-naphthalenedisulfonic acid (0.1 mol) was dispersed and dissolved in water (150 g), and diazotized in the same manner as described in Example 1. Magnesium oxide (a fine powdery reagent, 4.9 g) was added and suspended at 10° C. Then, while the temperature of the reaction mixture was maintained at 6–8° C., an aqueous sodium hypochlorite solution (68 g; available chlorine 13.3%) was added dropwise under vigorous agitation so as to adjust the pH to 8.8–9.7 over three and a half hours. A small amount of the diazo compound remaining in the aqueous mixture disappeared when the mixture was heated to 15° C., and the mixture assumed the form of a dark red transparent solution. Sodium 1,2-naphthoquinone-2-diazide-5-sulfonate contained in the solution was quantitated by high performance liquid chromatography. The conversion ratio (from the monosodium salt of 2-amino-1,5- naphthalenedisulfonic acid to sodium 1,2-naphthoquinone-2-diazide-5-sulfonate) was 84.5%.

A synthesis experiment as described above was performed, except that crystalline potassium iodide (0.7 g) was additionally added for dissolution after addition of magnesium oxide. The conversion ratio (from the monosodium salt of 2-amino-1,5-naphthalenedisulfonic acid to sodium 1,2naphthoquinone-2-diazide-5-sulfonate) was enhanced to 88.6%.

EXAMPLE 4

A monosodium salt of 2-amino-1,6-naphthalenedisulfonic acid (0.1 mol) and magnesium oxide (2.1 g) were added to water (220 g). The mixture was heated to 300 C. for dissolution. Sodium nitrite (7 g) was added and dissolved therein, and the mixture was cooled to 10° C. Separately, crushed ice (200 g) and 35% hydrochloric acid (27 g) were added to water (200 g). The aforementioned mixture of 2-amino- 1,6-naphthalenedisulfonate and sodium nitrite was added thereto with stirring to thereby obtain a suspension of 2diazo-1,6-naphthalenedisulfonate.

Magnesium oxide (5.7 g) was added to the suspension. An aqueous sodium hypochlorite solution (69 g; available chlorine 13.2%) was added dropwise at 15–20° C. for three and a half hours under vigorous agitation. When disappearance of 2-diazo-1,6-naphthalenedisulfonate was confirmed, 35% hydrochloric acid was added dropwise so as to adjust the pH to 6.1. The mixture was stirred gently for one hour at 15° C. The precipitate was filtered, washed with water, and dried to thereby obtain a 1,2-naphthoquinone-2-diazide-6-sulfonate in the form of fine powder. The theoretical yield is 75.2%.

A synthesis experiment as described above was performed except that potassium iodide (0.7 g) was additionally added to a mixture of magnesium oxide (5.7 g) and a suspension of 2-diazo-1,6-naphthalenedisulfonate. A 1,2-naphthoquinone-2-diazide-6-sulfonate was obtained in the form of fine powder. The theoretical yield is 81.5%.

EXAMPLE 5

A monosodium salt of 2-amino-1,5-naphthalenedisulfonic acid (0.1 mol) was diazotized in a manner similar to that in Example 1. An aqueous sodium carbonate solution was added dropwise at 10° C. so as to adjust the pH of the mixture to 6.6. Sodium carbonate (22 g) was added to water (64 g), and the resultant solution was added to an aqueous solution of sodium hypochlorite (62.2 g; available chlorine 12.8%) and mixed thoroughly. The resultant alkaline solution was added drowpwise to the above-mentioned diazotized solution at 14–15° C. over two hours. The mixture was analyzed in the same manner as described in Example 3. The conversion ratio (from the monosodium salt of 2-amino-1,5-naphthalenedisulfonic acid to sodium 1,2-naphthoquincne-2-diazide-5-sulfonate) was 88.3%.

A synthesis experiment as described above was performed except that after completion of diazotization an aqueous sodium carbonate solution was added dropwise so as to adjust the pH to 6.6 and sodium iodide (0.5 g) was added for dissolution. The conversion ratio (from the monosodium salt of 2-amino-1,5-naphthalenedisulfonic acid to sodium 1,2-naphthoquinone-2-diazide-5-sulfonate) was enhanced to 90.8%.

EXAMPLE 6

A monosodium salt of 2-amino-1,5-naphthalenedisulfonic acid (0.1 mol) was diazotized in exactly the same manner as in Example 3. The mixture was neutralized so as to adjust the pH to 6.6. An aqueous 35% sodium hydroxide solution (22.9 g) was added to an aqueous sodium hypochlorite solution (65 g; available chlorine 13.2%) and mixed homogeneously. The resultant mixture was added dropwise to the abovementioned diazotized solution at 8–9° C. over two hours. The resultant mixture was analyzed in the same manner as described in Example 3. The conversion ratio (from the monosodium salt of 2-amino-1,5-naphthalenedisulfonic acid to sodium 1,2-naphthoquinone-2-diazide-5-sulfonate) was 65.7%.

A synthesis experiment as described above was performed except that after completion of diazotization potassium iodide (0.5 g) was added for dissolution to the neutralized reaction mixture (pH 6.6). The conversion ratio (from the monosodium salt of 2-amino-1,5-naphthalenedisulfonic acid to sodium 1,2-naphthoquinone-2-diazide-5-sulfonate) was enhanced to 91.3%.

EXAMPLE 7

A monosodium salt of 2-amino-1,5-naphthalenedisulfonic acid (0.1 mol) was diazotized in exactly the same manner as in Example 1. The mixture was neutralized so as to adjust the pH to 6.6. Potassium permanganate (12.6 g) was dissolved in water (230 g), and the resultant solution was mixed with an aqueous 20% sodium hydroxide solution (30 g). While the pH and the temperature of the resultant mixture were maintained at 10–10.7 and 4–7° C. respectively, the mixture was added dropwise to the aforementioned aqueous diazotized compound solution over four hours. The mixture was analyzed in the same manner as described in Example 3. The conversion ratio (from the monosodium salt of 2-amino-1,5-naphthalenedisulfonic acid to 1,2-naphthoquinone-2-diazide-5-sulfonate) was 60.6%.

A synthesis experiment as described above was performed, except that potassium iodide (1.0 g) was added to and dissolved in the reaction mixture which had been diazotized and adjusted so as to have a pH 6.6. The conversion ratio (from the monosodium salt of 2-amino-1,5-naphthalenedisulfonic acid to 1,2-naphthoquinone-2-diazide-5-sulfonate) was enhanced to 65.1%.

EXAMPLE 8

A monosodium salt of 2-amino-1,5-naphthalenedisulfonic acid (0.1 mol) was diazotized in exactly the same manner as in Example 1. The mixture was neutralized so as to adjust the pH to 6.6. Magnesium oxide (a fine powdery reagent, 4.6 g) was added thereto and suspended. While the pH of the resultant mixture was maintained at 8.6–10.0 at 6–10° C. and under vigorous agitation, an aqueous 20% hydrogen peroxide solution (20 g) was added dropwise thereto for two hours. The mixture was analyzed in the same manner as described in Example 3. The conversion ratio (from the monosodium salt of 2-amino-1,5-naphthalenedisulfonic acid to 1,2-naphthoquinone-2-diazide-5-sulfonate) was 11.7%.

A synthesis experiment as described above was performed, except that sodium iodide (2 g) was added to and dissolved in the reaction mixture which had been diazotized and adjusted so as to have a pH 6.6. The conversion ratio (from the monosodium salt of 2-amino-1,5-naphthalenedisulfonic acid to 1,2-naphthoquinone-2-diazide-5-sulfonate) was enhanced to 47.2%.

EXAMPLE 9

An aqueous 35% sodium hydroxide solution (11.5 g) was added to water (220 g). 2-amino-1-naphthalenesulfonic acid (0.1 mol) was dissolved in the resultant solution. Sodium nitrite (7.05 g) was added to and dissolved in the solution, and the resultant mixture was cooled to 100 C. Separately, crushed ice (200 g) and 35% hydrochloric acid (26 g) were added to water (200 g). The aforementioned aqueous solution of 2-amino-1-naphthalenesulfonate salt and sodium nitrite was added thereto under stirring to thereby obtain a suspension of 2-diazo-1-naphthalenesulfonic acid. An aqueous 35% sodium hydroxide solution (6 g) was added dropwise to the suspension to adjust the pH to approximate 10. A mixture of an aqueous 35% sodium hydroxide solution (24.8 g) and an aqueous sodium hypochlorite solution (65.5 g; available chlorine 13.2%) was added dropwise at 15–20° C. over four hours to adjust the pH of the mixture to 10.0–10.8. Oxalic acid (0.3 g) was added thereto to adjust the pH to 4.5. Crystals that precipitated at 14° C. were collected by filtration, washed with water, and dried, to thereby obtain 1,2-naphthoquinone-2-diazide in the form of fine crystals. The theoretical yield was 43%.

A synthesis experiment as described above was performed, except that an aqueous 35% sodium hydroxide solution (6 g) was added dropwise to a suspension of 2-diazo-1-naphthalenesulfonic acid so as to adjust the pH to approximate 10 and that sodium iodide (1.0 g) was subsequently added. 1,2-naphthoquinone-2-diazide was obtained in the form of fine crystals. The theoretical yield was 89%.

As described herein above, the present invention produces 1,2-naphthoquinone-2-diazide or a sulfo-substituted compound thereof at an excellent yield by bringing 2-diazo-1-naphthalenesulfonic acid or a sulfo-substituted compound thereof into contact with an aqueous alkaline solution.

What is claimed is:

1. A method for producing a 1,2-naphthoquinone-2-diazide derivative, which method comprises bringing a 2-diazo-1-naphthalenesulfonic acid derivative into contact with an aqueous alkaline solution containing at least one substance selected from iodine and iodine compounds.

2. A method for producing a 1,2-naphthoquinone-2-diazide derivative according to claim 1, wherein the aqueous alkaline solution contains iodine.

3. A method for producing a 1,2-naphthoquinone-2-diazide derivative according to claim 1, wherein the aqueous alkaline solution comprises a mixture of an alkaline solution and iodine dissolved in an organic solvent which solvent is hardly soluble in water and which exhibits little reactivity with iodine.

4. A method for producing a 1,2-naphthoquinone-2-diazide derivative according to claim 1, wherein the aqueous alkaline solution containing at least one substance selected from iodine and iodine compounds further contains an oxidizing agent.

5. A method for producing a 1,2-naphthoquinone-2-diazide derivative according to claim 4, wherein the iodine compounds are selected from iodides of metals including lithium, sodium, potassium, magnesium, calcium, and aluminum; hypoiodite and iodate salts; hydroiodides of amines including trimethylamine and triethylamine; iodide of tetraalkylammoniums including tetramethylammonium and tetraethylammonium; iodine halides including iodine chloride, iodine bromide, and iodine trichloride; and iodine oxides including diiodine tetraoxide and diiodine pentaoxide.

6. A method for producing a 1,2-naphthoquinone-2-diazide derivative according to claim 4, wherein the oxidizing agent is at least one member selected from among chlorine, bromine, sodium hypochlorite, potassium hypochlorite, calcium hypochlorite, magnesium hypochlorite, sodium hypobromite, potassium hypobromite, hydrogen peroxide, potassium permanganate, and sodium permanganate.

7. A method for producing a 1,2-naphthoquinone-2-diazide derivative according to any one of claims 1 through 6, wherein the 2-diazo-1-naphthalenesulfonic acid derivative is 2-diazo-1-naphthalenesulfonic acid, a sulfo-substituted compound thereof or a salt thereof.

8. A method for producing a 1,2-naphthoquinone-2-diazide derivative according to any one of claims 1 through 7, wherein the 1,2-naphthoquinone-2-diazide derivative is any one of 1,2-naphthoquilnbne-2-diazide, and sodium, potassium, magnesium, calcium, barium, aluminium, trimethylammonium, triethylammonium, tetramethylammonium, or tetraethylammonium salts of the following sulfonic acids: 1,2-naphthcquinone-2-diazide-5-sulfonic acid, 1,2naphthoquinone-2-diazide-6-sulfonic acid, 1,2-naphthoquinone-2-diazide-7-sulfonic acid, 1,2-naphthoquinone-2-diazide-5,6-disulfonic acid, 1,2-naphthoquinone-2-diazide-5,7-disulfonic acid, or 1,2-naphthoquinone-2-diazide-5,8-disulfonic acid.

* * * * *